United States Patent [19]

Masaki et al.

[11] 4,359,989

[45] Nov. 23, 1982

[54] SYSTEM FOR FEEDBACK CONTROL OF AIR-FUEL MIXING RATIO IN INTAKE SYSTEM OF INTERNAL COMBUSTION ENGINE

[75] Inventors: Kenji Masaki, Yokohama; Kohki Sone, Tokyo; Sadao Takase, Yokohama, all of Japan

[73] Assignee: Nissan Motor Co., Ltd., Yokohama, Japan

[21] Appl. No.: 161,405

[22] Filed: Jun. 20, 1980

[30] Foreign Application Priority Data

Jun. 22, 1979 [JP] Japan .................................. 54-78698

[51] Int. Cl.³ ........................ F02D 33/00; F02M 7/24
[52] U.S. Cl. ................................ 123/438; 204/195 S
[58] Field of Search .............................. 123/438, 440; 204/195 S, 1 S

[56] References Cited

U.S. PATENT DOCUMENTS

| | | | |
|---|---|---|---|
| 3,616,274 | 10/1971 | Eddy | 204/1 T |
| 4,050,425 | 9/1977 | Holleboom | 123/438 |
| 4,156,413 | 5/1979 | Taplin | 123/119 EC |
| 4,207,159 | 6/1980 | Kimura et al. | 204/195 S |
| 4,212,273 | 7/1980 | Maruoka | 123/438 |
| 4,217,869 | 8/1980 | Masaki | 123/438 |
| 4,224,113 | 9/1980 | Kimura et al. | 204/1 T |
| 4,264,425 | 4/1981 | Kimura et al. | 204/195 S |

FOREIGN PATENT DOCUMENTS

| | | | |
|---|---|---|---|
| 2743367 | 3/1978 | Fed. Rep. of Germany | 123/438 |
| 2745208 | 4/1978 | Fed. Rep. of Germany | 123/438 |
| 2382583 | 9/1978 | France | 123/438 |
| 2393302 | 12/1978 | France | 123/438 |
| 2440552 | 5/1980 | France | 204/1 T |
| 1511467 | 5/1978 | United Kingdom | 123/438 |
| 1568426 | 5/1980 | United Kingdom | 123/438 |

*Primary Examiner*—G. L. Kaplan
*Attorney, Agent, or Firm*—Schwartz, Jeffery, Schwaab, Mack, Blumenthal & Koch

[57] ABSTRACT

A feedback control system using an oxygen-sensitive air/fuel ratio sensor which is disposed in induction passage for an IC engine downstream of a fuel supply device with the provision of an ignition means to burn a fractional portion of an air-fuel mixture in the induction passage such that the oxygen-sensitive sensor is exposed to a resultant combustion gas. The sensor is of the concentration cell type having a layer of solid electrolyte such as zirconia provided with two electrode layers, and constant DC current is supplied to this sensor to cause migration of oxygen ions through the solid electrolyte layer, whereby this sensor exhibits a slope output characteristic and can detect air/fuel ratios either above or below a stoichiometric ratio or exhibits an on-off characteristic and can detect the stoichiometric ratio depending on the intensity and flow direction of the current. Owing to reduced overall length of the closed-loop, this control system can accomplish correction of a deviated mixing ratio in a shortened period of time.

11 Claims, 15 Drawing Figures

SYSTEM FOR FEEDBACK CONTROL OF AIR-FUEL MIXING RATIO IN INTAKE SYSTEM OF INTERNAL COMBUSTION ENGINE

FIELD OF THE INVENTION

This invention relates to a feedback control system for precisely controlling the mixing ratio of an air-fuel mixture to be supplied to an internal combustion engine by using a gas sensor which is sensitive to a specific component of a combustion gas produced from the air fuel mixture and can provide a feedback signal indicative of an actual mixing ratio of the air-fuel mixture.

DESCRIPTION OF THE PRIOR ART

Concerning internal combustion engines particularly in automobiles, one recently developed important technique is to perform feedback control of the fuel feed rate by using an exhaust sensor. The sensor is sensitive to a specific component of the exhaust gas and provides an electrical signal indicative of the actual composition of an air-fuel mixture supplied to the engine. The feedback control operates the engine with an air-fuel mixture of a precisely controlled mixing ratio thereby enabling satisfactory purification of the exhaust gas and enhancing the efficiency of the engine. This technique has already been put into practical use and applied to both electronically controlled fuel injectors and carburetors.

As the aforementioned exhaust sensor, amost exclusively use has been made of an oxygen sensor of the oxygen concentration cell type fundamentally comprised of a layer of an oxygen ion conductive solid electrolyte such as zirconia stabilized with calcia, a measurement electrode layer, usually of platinum, formed porously on one side of the solid electrolyte layer and a reference electrode layer formed on the other side. This oxygen sensor generates an electromotive force when there is a difference between a reference partial oxygen pressure maintained on the reference electrode side and a variable oxygen partial pressure developed on the measurement electrode side. As shown in FIG. 1, usually the solid electrolyte layer is made to take the shape of a tube 12 having a closed end so that the reference electrode layer 14 on the inside can be exposed to air utilized as the source of the reference oxygen partial pressure while the measurement electrode layer 16 on the outside is exposed to an exhaust gas flowing in an exhaust pipe. In conventional feedback control systems for the control of the air/fuel ratio, the electromotive force generated by the oxygen sensor installed in the exhaust pipe is put into an electronic control circuit, which provides a control signal to a fuel supply means based on the result of a comparison between a predetermined reference voltage and the magnitude of the electromotive force.

The magnitude of an electromotive force generated by this oxygen sensor 10 exposed to the exhaust gas is indicative of the air/fuel ratio of a mixture supplied to the engine but is not proportional to the air/fuel ratio. As shown in FIG. 2, the electromotive force remains practically constantly at a high level while the air/fuel ratio is below a stoichiometric air-fuel ratio (about 14.7 for air-gasoline mixture), that is, while a rich mixture is supplied to the engine and, in contrast, remains practically constantly at a very low level while the air/fuel ratio is above the stoichiometric ratio, that is, while a lean mixture is supplied to the engine. And, a great and sharp change occurs in the magnitude of the electromotive force upon the occurrence of a change in the air/fuel ratio across the stoichiometric ratio. Therefore, the use of this oxygen sensor is quite suitable where the aim of the control is the production of a stoichiometric air/fuel ratio as in the case of using a so-called three-way catalyst which catalyzes both reduction of NOx and oxidation of CO and HC (unburned hydrocarbons). The three-way catalyst exhibits the highest conversion efficiency in an exhaust gas produced by combustion of a stoichiometric air-fuel mixture. However, when the control point is an air/fuel ratio deviates substantially from the stoichiometric ratio this oxygen sensor 10 becomes unserviceable.

In the current automobile industry the most prevailing method for purification of exhaust gases is the use of an oxidation catalyst in combination with a certain measure for reducing the emission of NOx, such as the recirculation of a portion of the exhaust gas. The use of a three-way catalyst has only a limited share primarily because this catalyst requires rhodium which is a costly material and is not produced in sufficient abundance to fill the demand of a huge number of automobiles throughout the world. The use of a thermal reactor is not prevalent either because of disadvantages such as increase in the fuel consumption by reason of the need of operating the engine with a rich mixture and the need for using a costly heat- and corrosion-resistant alloy as a structural material for the reactor.

In the case of using an oxidation catalyst, usually it becomes necessary to employ a non-stoichiometric air-fuel mixture with the maintenance of an optimal air/fuel ratio to allow the catalyst to exhibit its maximal conversion efficiency. Accordingly it is desired to perform feedback control of the air/fuel ratio, but this desire can hardly be met because there is no practicable exhaust sensor by which air/fuel ratio values different from the stoichiometric ratio can be detected. Therefore, immense effort has been devoted to the development of most efficient and durable catalyst converters containing an oxidation catalyst and fuel supply devices to be combined with such catalytic converters for each model of recently produced automobiles. Furthermore, mass production of such devices and major component parts for the devices is performed under extremely strict quality control in order to ensure optimum performance of every product and minimize the differences in performance among the individual products. In addition, during the assembly of the automobiles much effort is directed to providing the best match between the engine and fuel supply device in each car because not only the exhaust-purifying efficiency but also the mechanical and thermal efficiencies of the engine are greatly affected by the degree of such matching. Of course, these endeavors inevitably and considerably raise the cost of production.

Therefore, there is an earnest demand for a novel gas-sensing technique which enables the detection of every air/fuel ratio value in the practicable range.

In this regard, U.S. Patent Application Ser. No. 28,747 filed Apr. 10, 1979, now U.S. Pat. No. 4,224,113, proposes to detect air/fuel ratio values of either a lean mixture or a rich mixture supplied to an engine by means of an oxygen sensing device of a modified concentration cell type which exhibits a desirable output characteristic when disposed in an exhaust gas and supplied with a constant DC current of an adequate intensity. The particulars of this oxygen sensing device will be described hereinafter.

When feedback control of air-fuel mixing ratio is carried out by using either a conventional oxygen sensor of the type illustrated in FIG. 1 or the device proposed in U.S. Patent Application Ser. No. 28,747, a problem that has been left unsolved is the existence of a considerable time lag in either the generation of a feedback signal after the generation of a control signal or return of an undesirable air/fuel ratio to the target of control after the commencement of a corrective action. This time lag results because the closed-loop of the control system has a considerable length and includes a plurality of functional elements. Because of the existence of such time lag, the air-fuel mixing ratio cannot be maintained exactly at a preset value and continues to exhibit oscillatory fluctuations as illustrated in FIG. 3. Numerically, the range of air/fuel ratio fluctuations is about ±0.25 with respect to the intended stoichiometric ratio, 14.7. The particulars of the aforementioned time lag will be explained with respect to a conventional air/fuel ratio control system shown in FIG. 4.

In FIG. 4, numeral 20 indicates a principal part of a gasoline engine equipped with a carburetor 18. A main fuel nozzle 28 as the terminal of a main fuel passage 27 in the carburetor 18 opens into an induction passage 22 at a venturi section 26 upstream of a throttle valve 24. A main air bleed 30 is provided to the fuel passage 27 in the usual manner. In addition, an auxiliary air bleed 32 is provided to the same fuel passage 27, and an electromagnetic flow control valve 34 of the on-off functioning type is associated with the auxiliary air bleed 32 in order to control the admission of air through this air bleed 32 in response to a control signal supplied from a control circuit 40. An oxygen sensor 38 of the type as shown in FIG. 1 is installed in an exhaust passage 36 to provide a feedback signal to the control circuit 40.

While the feedback signal indicates the supply of a rich mixture to the engine 20, the control circuit 40 commands the electromagnetic valve 34 to increase the proportion of its open-duration to closed-duration thereby to admit a relatively large quantity of air into the fuel passage 27 through the auxiliary air bleed 32 until the feedback signal indicates rise in the air/fuel ratio to the intended stoichiometric ratio. While the feedback signal indicates the supply of a lean mixture, the electromagnetic valve 34 is commanded to decrease or interrupt the admission of air through the auxiliary air bleed 32.

During a deviation correcting process in this feedback control system there is a time lag in the response or function of each element of the control system. The following Table 1 presents experimentally confirmed values of such time lag with respect to a 2-liter 6-cylinder automotive gasoline engine operated at a constant speed of 2000 r.p.m. under a load condition expressed by an intake vacuum of −200 mmHg. The air/fuel ratio was varied within the range of 12.7–16.7.

TABLE 1

| | Time Lag | |
|---|---|---|
| Direction of Change of Air-Fuel Mixing Ratio | Low → High (Rich → Lean) | High → Low (Lean → Rich) |
| control circuit-EM valve | 6 ms | 4 ms |
| EM valve-main fuel nozzle | 4 ms | 3 ms |
| main nozzle-intake valve | 15 ms | 15 ms |
| waiting for opening of intake valve | 0–60 ms | 0–60 ms |
| combustion chamber | 32 ms | 32 ms |

TABLE 1-continued

| | Time Lag | |
|---|---|---|
| exhaust valve-O$_2$—sensor | 6 ms | 6 ms |
| response of O$_2$—sensor | 20 ms | 15 ms |
| total time lag in response | 143 ms (max.) | 135 ms (max.) |
| time required to correct deviated mixing ratio to stoichiometric ratio by continuing correcting process | about 250 ms | about 210 ms |
| total time lag in control | about 393 ms (max.) | about 345 ms (max.) |

In Table 1, "total time lag in response" refers to a time period from a time point at which the oxygen sensor 38 produces a signal indicating deviation of the air-fuel mixing ratio from the stoichiometric ratio to a time point at which the oxygen sensor 38 produces a signal indicating the arrival of exhaust gas resulting from combustion of a corrected air-fuel mixture at the location of the oxygen sensor 38. This time period will be called simply "response lag". However it does not mean that the deviated mixing ratio is corrected to the intended stoichiometric ratio within this time period. The control circuit 40 is so constructed as to perform, for example, a proportional-and-integral control process such that the mixing ratio is gradually raised (or lowered) towards the stoichiometric ratio. Although the stoichiometric ratio is reached in a short while, usually the control circuit 40 does not instantaneously stop performing the mixing ratio-raising control process but continues the same process until the output voltage of the oxygen sensor 38 becomes below a predetermined reference voltage. At this time point, the control circuit 40 commences to put out an inverted control signal to lower the excessively raised mixing ratio. Therefore, it takes about 250 ms (or about 210 ms) to correct the once deviated mixing ratio to the stoichiometric ratio in addition to the aforementioned "response lag". The sum of the "response lag" and the additionally required time (250 ms or 210 ms) will be called "control lag".

In the automobile industry it is also an important technological task to shorten the "control lag" in the above described type of feedback control systems, and much effort have been made to improve the responsiveness of the respective elements of the control system and in parallel shorten the overall length of the closed-loop.

SUMMARY OF THE INVENTION

It is an object of the present invention to provide a system for feedback control of the air-fuel mixing ratio in an internal combustion engine, which system allows any air/fuel ratio value within the range practical for gasoline engines and Diesel engines to be employed as the target of control and, as an additional advantage, can perform the control with improved precision and shortened "response lag" and "control lag".

A feedback control system according to the invention controls the mixing ratio of an air-fuel mixture flowing in an induction passage for an internal combustion engine. This control system comprises an electrically controllable fuel supply means for supplying fuel into the induction passage, an oxygen-sensitive air/fuel ratio sensor which is disposed in the induction passage at a section downstream of the fuel supply means, a control circuit for providing a control signal to the fuel supply means based on a feedback signal produced by the air/fuel ratio sensor to correct a deviation of the air-fuel mixing ratio from a predetermined mixing ratio indicated by the feedback signal. The air/fuel ratio sensor comprises a layer of an oxygen ion conductive solid electrolyte formed on a substrate and two electrode layers formed on the solid electrolyte layer. The control system further comprises an ignition means for burning a fractional portion of the air-fuel mixture flowing in the induction passage such that the air/fuel ratio sensor is exposed to a resultant combustion gas and a power supply means for forcing a constant DC current of a predetermined intensity to flow through the solid electrolyte layer of the sensor between the two electrode layers thereby selectively affording the air/fuel ratio sensor exposed to the combustion gas with one of an on-off type output characteristic, which means that the magnitude of the output of the sensor undergoes a sharp change between a maximally high level and a minimally low level when the air-fuel mixing ratio changes across a stoichiometric air/fuel ratio, a first slope output characteristic, which means that the magnitude of the output of the sensor gradually varies as the air-fuel mixing ratio varies but remains above the stoichiometric ratio, and a second slope output characteristic which means that the magnitude of the output of the sensor gradually varies as the air-fuel mixing ratio varies but remains below the stoichiometric ratio.

When the first or second slope output characteristic is afforded to the air/fuel ratio sensor, preferably another (second) oxygen-sensitive air/fuel ratio sensor which exhibits the aforementioned on-off type output characteristic when exposed to the combustion gas is disposed in the induction passage at a location close to the aforementioned (first) sensor such that the second sensor too is exposed to the aforementioned combustion gas, and the control circuit is made to have an additional function of ascertaining whether the output of the first sensor is truly attributed to the slope output characteristic of this sensor based on the level of the simultaneously produced output of the second sensor. In this case, it is preferable that the first and second sensors are of the same type and constructed as a single device having two layers of the solid electrolyte on a single substrate.

Since the overall length of the closed-loop of the feedback control system of the invention becomes considerably smaller than that in a conventional air/fuel ratio control system, the control system of the invention operates with shortened "control lag" and enhanced precision of control. Moreover, this control system is practicable irrespective of the value of the air-fuel mixing ratio taken as the target of control.

DETAILED DESCRIPTION OF THE INVENTION

First the construction and function of a recently developed air/fuel ratio detection device, which is described in the aforementioned U.S. patent application Ser. No. 28,747 and used in the present invention in a new manner, will be described with reference to FIGS. 5–7.

Figure 5:
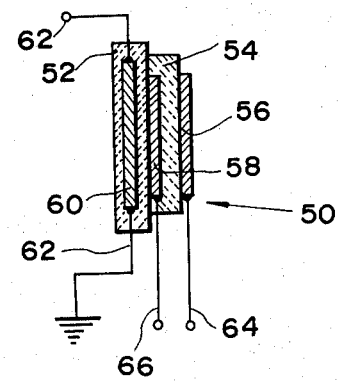
FIG. 5 shows schematically and sectionally a fundamental construction of an oxygen sensing element used in the present invention.

FIG. 5 shows an oxygen sensing element 50 as a principal component of the air/fuel ratio detection device. The element 50 has a ceramic substrate 52 such as of alumina, and a microscopically porous layer 54 of an oxygen ion conductive solid electrolyte such as $ZrO_2$ stabilized with $Y_2O_3$ is formed on one side of the substrate 52. A first platinum electrode layer 56 is formed on the outer side of the solid electrolyte layer 54. This electrode layer 56 has a gas permeably porous structure so that a gas subject to measurement not only contacts the outer surface of this electrode layer 56 but also diffuses into the solid electrolyte layer 54. A second platinum electrode layer 58 is formed on the other side of the solid electrolyte layer 54 so as to be sandwiched between the substrate 52 and the solid electrolyte layer 54 and, macroscopically, completely shielded from an environmental atmosphere by the substrate 52 and the solid electrolyte layer 54. It will be understood that the three layers 54, 56 and 58 constitute an oxygen concentration cell. Usually each of these three layers 54, 56, 58 is formed as a thin, film-like layer. An electric heater element 60 is embedded in the substrate 52 because the concentration cell does not function efficiently unless it is maintained at a sufficiently high temperature. Indicated at 62 are leads to supply a heating current to the heater element 60, and at 64 and 66 are leads respectively attached to the first and second electrode layers 56 and 58.

Figure 7:
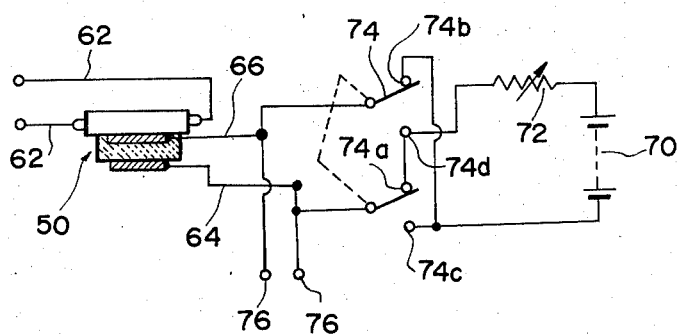
FIG. 7 is a diagrammatic illustration of an air/fuel ratio detection device comprising the oxygen sensing element of FIG. 5.

To detect the mixing ratio of an air-fuel mixture subjected to combustion in a combustor such as combustion chambers of an internal combustion engine, the oxygen sensing element 50 is entirely disposed in a combustion gas produced by the combustion and, instead of using a reference oxygen source such as air, a DC power supply 70 is connected to the leads 64 and 66, that is, to the first and second electrode layers 56 and 58 of this element, as shown in FIG. 7, to force a constant DC current of an adequate intensity (e.g. 3–10 $\mu$A) to flow through the solid electrolyte layer 54 between the two electrode layers 56 and 58. In FIG. 7, indicated at 72 is a variable resistor to regulate the intensity of the current. The purpose of supplying an electric current to the oxygen sensing element 50 is to establish a reference oxygen partial pressure at the interface between the second electrode layer 58 and the solid electrolyte layer 54 as described hereinafter. Accordingly the second electrode layer 58 will be referred to as reference electrode layer, while the first electrode layer 56 which is directly exposed to the combustion gas will be called measurement electrode layer. The leads 64 and 66 are connected also to output terminals 76 where an electromotive force generated across the solid electrolyte layer 54 between the two electrode layers 56 and 58 is measured.

The magnitude of this electromotive force depends on the air/fuel ratio of the air-fuel mixture subjected to combustion, and the manner of the dependence is determined fundamentally by the direction of flow of the current supplied to the oxygen sensing element 50. In FIG. 7 a double-pole double-throw switch 74 is used to connect the DC power source 70 to the oxygen sensing element 50, and illustrated is a case where the measurement and reference electrode layers 56 and 58 are connected respectively to the positive and negative terminals of the DC power supply 70 by utilizing contacts 74a and 74b of the switch 74 so that the current flows through the solid electrolyte layer 54 from the measurement electrode layer 56 towards the reference electrode layer 58. In this case, the oxygen sensing element 50 exhibits an output characteristic as represented by curve A in FIG. 6 for the following reason.

While a fuel-rich mixture is subjected to combustion, the combustion gas contains considerable amounts of CO and HC. Since the measurement electrode layer 56 is made of platinum which acts as a catalyst, CO and HC in the combustion gas undergo oxidation reactions at the surface of this electrode layer 56 with $O_2$ contained in the combustion gas. Therefore, a very low oxygen partial pressure is maintained on the measurement electrode side of the solid electrolyte layer 54. The combustion gas diffuses through the porous solid electrolyte layer 54 and reaches the reference electrode layer 58. Since the reference electrode layer 58 is connected to the negative terminal of the DC power source 70, there is a tendency that oxygen is ionized at this electrode layer 58 followed by outflow of the ionized oxygen towards the measurement electrode layer 56. This will result in further lowering of oxygen partial pressure at the reference electrode layer 58, but actually this phenomenon is almost negligible because little oxygen molecules are present in the combustion gas diffused to the reference electrode layer 58 after the aforementioned oxidation reactions at the measurement electrode layer 56. Therefore, an oxygen partial pressure on the reference electrode side of the solid electrolyte layer 54 does not significantly differ from the oxygen partial pressure on the measurement electrode side, so that the output voltage of the oxygen sensing element 50 becomes very low and does not significantly vary even though changes occur in the air/fuel ratio of the rich mixture.

When the air/fuel ratio of the mixture subjected to combustion increases above a stoichiometric ratio (about 14.7 for an air-gasoline mixture), the total amount of CO and HC in the combustion gas exhibits an abrupt and great decrease. Then the consumption of oxygen in the aforementioned oxidation reactions at the surface of the measurement electrode layer 56 becomes insignificant, so that the oxygen partial pressure at the interface between the solid electrolyte layer 54 and this electrode layer 56 becomes nearly equal to the oxygen partial pressure in the combustion gas. At the reference electrode layer 58, there occurs ionization of $O_2$ contained in the combustion gas, and $O^{2-}$ ions formed at this electrode layer 58 continue to migrate through the solid electrolyte layer 54 toward the measurement electrode layer 56. As the result, an oxygen partial pressure on the reference electrode side of the solid electrolyte layer 54 becomes considerably lower than the oxygen partial pressure in the combustion gas while the air/fuel ratio is higher than but not greatly deviated from the stoichiometric ratio, and, therefore, the oxygen sensing element 50 produces a maximally high output voltage. However, the oxygen partial pressure at the reference electrode layer 58 gradually becomes higher to near the oxygen partial pressure in the combustion gas as the air/fuel ratio of the mixture (now a lean mixture) becomes higher, because the rate of diffusion of $O_2$ through the solid electrolyte layer 54 towards the reference electrode layer 58 gradually increases as the air-fuel mixture becomes leaner whereas the rate of ionization of oxygen at the reference electrode layer 58 is determined by the intensity of the current supplied to the oxygen sensing element 50 and accordingly remains constant. Consequently, the output voltage of the oxygen sensing element 50 exhibits a gradual decrease as the air/fuel ratio increases. That is, this element 50 exhibits a slope output characteristic when disposed in a combustion gas produced by combustion of a lean mixture with the supply of a constant current of an adequate intensity to flow from the measurement electrode layer 56 towards the reference electrode layer 58. If, however, the intensity of the constant current is made above a certain critical value (e.g. about 15 $\mu$A), the output voltage of the same element 50 remains constantly at a maximally high level while the air/fuel ratio varies but remains above the stoichiometric ratio because the rate of ionization of oxygen at the reference electrode layer 58 is so enhanced that the oxygen partial pressure at this electrode layer 58 is hardly influenced by changes in the rate of diffusion of gaseous oxygen through the solid electrolyte layer 54. In such a case, therefore, this oxygen sensing element 50 exhibits an on-off type output characteristic represented by a curve almost symmetrical with the characteristic curve of FIG. 2 exhibited by the conventional oxygen sensor 10 of FIG. 1 and becomes useful for detection of a stoichiometric air/fuel ratio.

Figure 6:
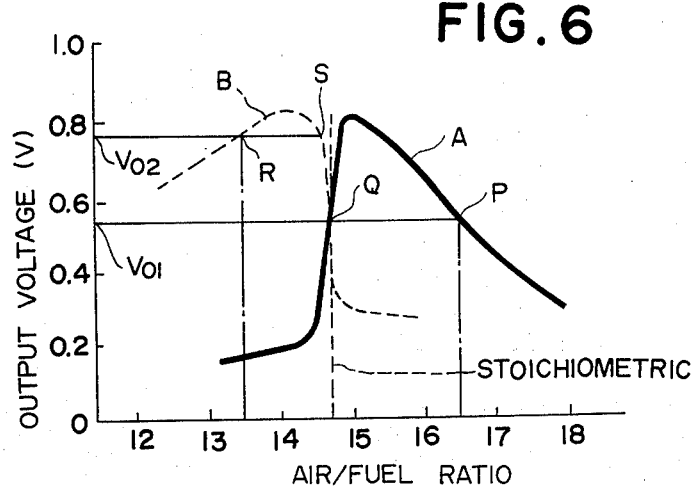
FIG. 6 shows output characteristics of the oxygen sensing element of FIG. 5 when used in engine exhaust gases.

When the measurement and reference electrode layers 56 and 58 of the oxygen sensing element 50 in FIG. 7 are respectively connected to the negative and positive terminals of the DC power supply 70 by utilizing contacts 74c and 74d of the switch 74 so that a constant current flows through the solid electrolyte layer 54 from the reference electrode layer 58 towards the measurement electrode layer 56, the element 50 in a combustion gas exhibits an output characteristic represented by curve B in FIG. 6.

In this case there occur ionization of oxygen at the measurement electrode layer 56 and migration of $O^{2-}$ ions through the solid electrolyte layer 54 from the measurement electrode layer 56 towards the reference electrode layer 58. While a lean mixture is subjected to combustion, the difference in oxygen partial pressure between the measurement electrode side and reference electrode side of the solid electrolyte layer 54 is very small because oxygen in the combustion gas is scarcely consumed in oxidation reactions and the effect of the inflow of oxygen ions to the reference electrode layer 58 is small compared with diffusion of a relatively large quantity of gaseous oxygen through the solid electrolyte layer 54. Accordingly the output voltage of the oxygen sensing element 50 remains nearly constantly at a very low level.

Figure 1:
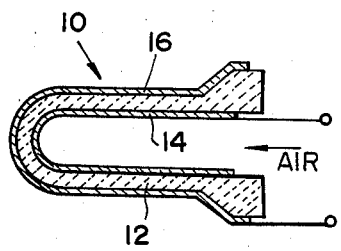
FIG. 1 is a schematic and sectional view of a conventional oxygen sensor.

When the air/fuel ratio becomes below the stoichiometric ratio, the consumption of oxygen in oxidation reactions of CO and HC at the surface of the measurement electrode layer 56 becomes significant, so that the oxygen partial pressure on the measurement electrode side becomes far lower than the oxygen partial pressure on the reference electrode side. Therefore, the output voltage of the element 50 rises to a maximally high level. As the air/fuel ratio further decreases, the oxygen partial pressure at the reference electrode layer 58 gradually lowers because ionization of oxygen at the measurement electrode layer 56 and resulting inflow of oxygen ions to the reference electrode layer 58 become less significant compared with greatly decreasing diffusion of gaseous oxygen through the solid electrolyte layer 54 to the reference electrode layer 58. Consequently the output voltage of the oxygen sensing element 50 exhibits a gradual decrease as the air/fuel ratio decreases. That is, in this case the element 50 exhibits a slope output characteristic when disposed in a combustion gas produced by combustion of a fuel-rich air-fuel mixture. If, however, the intensity of the constant current is made above a certain critical value the output voltage of the same element 50 remains constantly at a maximally high level while the air/fuel ratio varies but remains below the stoichiometric ratio because of greatly augmented inflow of oxygen ions to the reference electrode layer 58. This means that the oxygen sensing element 50 can be made to exhibit an on-off type output characteristic almost similar to that of the conventional oxygen sensor 10 of FIG. 1 represented by the curve of FIG. 2.

Figure 2:
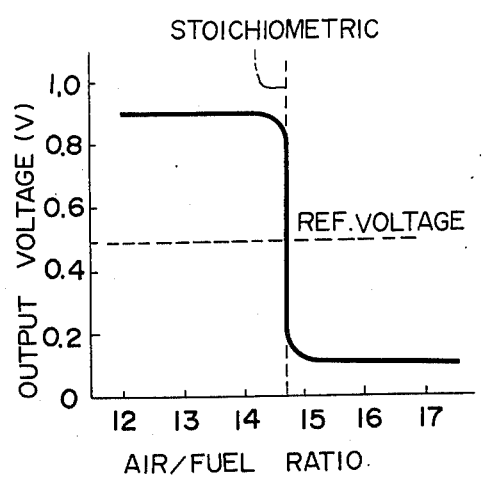
FIG. 2 shows an output characteristic of the oxygen sensor of FIG. 1 when used in an engine exhaust gas.
Figure 3:
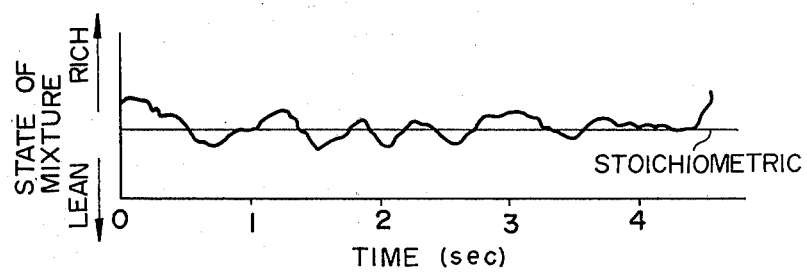
FIG. 3 is a chart illustrating the manner of fluctuations of the mixing ratio of an air-fuel mixture supplied to an internal combustion engine when the mixing ratio is controlled by a conventional feedback control system.

Thus it is possible to make the oxygen sensing element 50 exhibit any one of the three types of output characteristics respectively represented by the curves A and B of FIG. 6 and the curve of FIG. 2.

According to the present invention, an induction passage for an internal combustion engine is provided with a sensor of the type shown in FIGS. 5 and 7 in combination with an ignition device to burn a fractional portion of an air-fuel mixture in the induction passage such that the oxygen sensing element functions in a resultant combustion gas, and the output of the oxygen sensing element is used as a feedback signal indicative of an actual mixing ratio of the air-fuel mixture. Therefore, the closed-loop in a feedback control system according to the invention includes neither the combustion chambers of the engine nor any part of the exhaust system.

Figure 8:
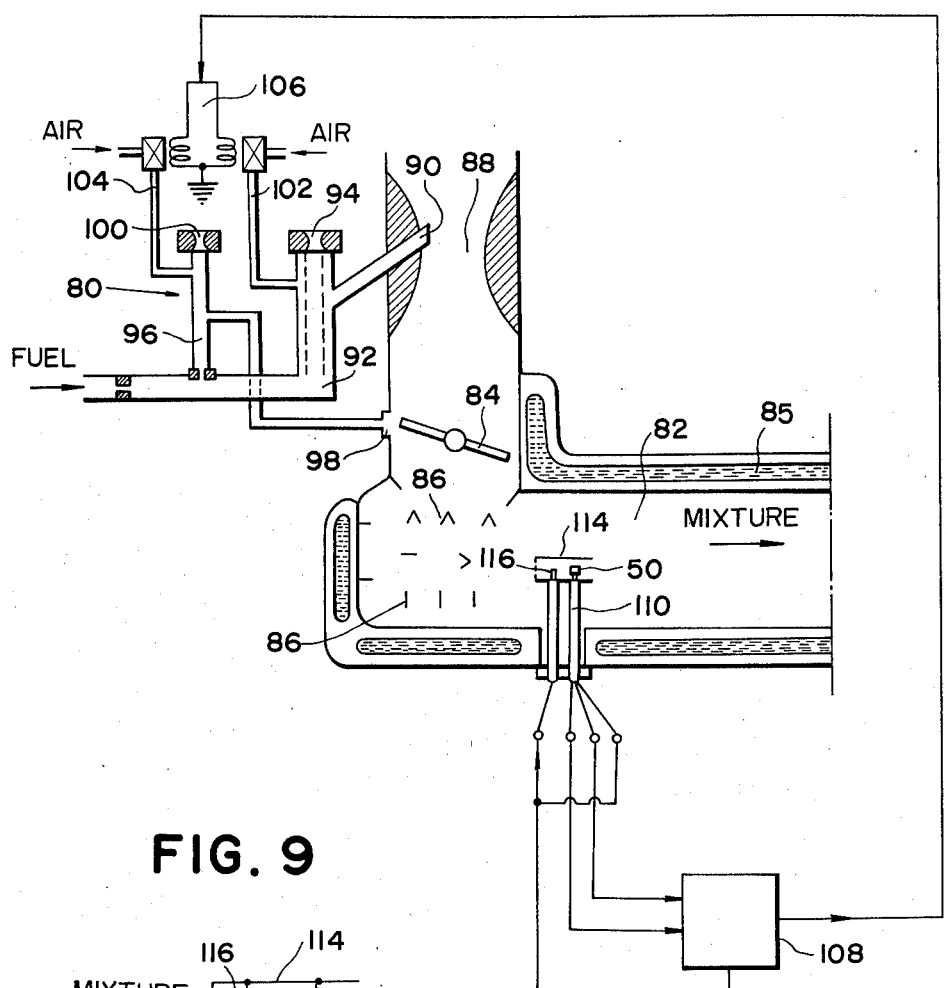
FIG. 8 is a sectional view of a part of an intake system for a gasoline engine, which intake system is provided with an air/fuel ratio control system according to the invention.

FIG. 8 shows an embodiment of the present invention. Indicated generally at 80 is a carburetor provided to an induction passage 82 for an automotive gasoline engine (not illustrated). Downstream of a throttle valve 84, the induction passage 82 is surrounded by a heating passage 85 through which flows engine cooling water in a heated state to promote atomization of fuel in an air/fuel mixture flowing towards the combustion chambers. A main fuel nozzle 90 as the terminal of a main fuel passage 92 in the carburetor 80 opens into the induction passage 82 at a venturi section 88 upstream of the throttle valve 84, and a slow-port 98 as the terminal of a slow-speed fuel passage 96 opens into the induction passage 82 at a section near the throttle valve 84. The main fuel passage 92 is provided with a main air bleed 94 in the usual manner, and the slow-speed fuel passage 96 is also provided with a main air bleed 100. In addition, an auxiliary air bleed 102 is provided to the main fuel passage 92 and similarly an auxiliary air bleed 104 to the slow-speed fuel passage 96. An electromagnetic flow control valve 106 of the on-off functioning type is associated with the two auxiliary air bleeds 102 and 104 so as to simultaneously control the admission of air through these auxiliary air bleeds 102 and 104 in response to a control signal supplied from a control unit 108.

At a section downstream from the throttle valve 84, an air/fuel ratio sensor 110 comprising the oxygen sensing element of FIG. 5 is inserted into the induction passage 82, and baffle plates 86 are arranged between the throttle valve 84 and the sensor 110 to completely homogenize the air-fuel mixture before its arrival at the location of the sensor 110. The control unit 108 supplies a constant DC current of a predetermined intensity to the oxygen sensing element 50 of the sensor 110 so as to make the element 50 exhibit a selected type of output characteristic. The control unit 108 supplies a heating current, too, to the element 50 and receives the output voltage of the element 50 to produce a control signal for the control of the proportion of on-period to off-period of the electromagnetic valve 106 so as to realize a preset air-fuel mixing ratio by utilizing the output of the element 50 as a feedback signal indicative of actual mixing ratio of the air-fuel mixture.

Figure 9:
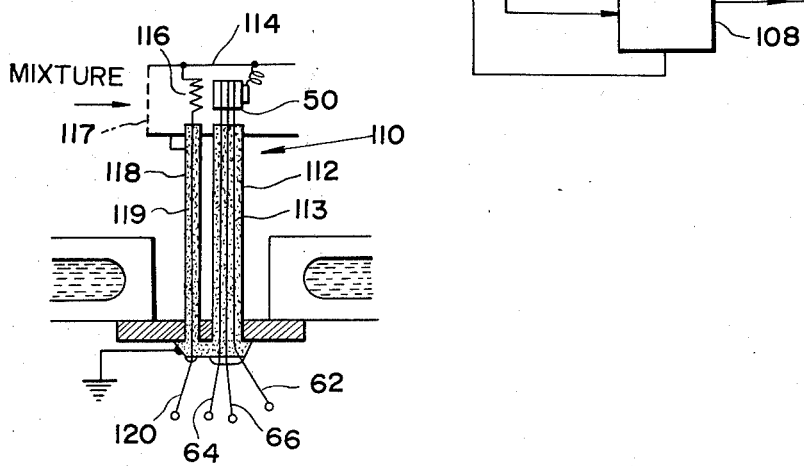
FIG. 9 shows schematically and sectionally a principal part of an air/fuel ratio detection device employed in the control system in FIG. 8.

Referring also to FIG. 9, the oxygen sensing element 50 is disposed in a small metal tube 114 which is held by a tubular metal support 112 so as to lie in a central region of the induction passage 82 along the direction of the flow of the air-fuel mixture. Leads 62, 64, 66 of the sensor 110 extend through the tubular support 112, and the interior of the support 112 is filled with an insulating material 113. In the metal tube 114, there is a heater element 116 positioned upstream of the oxygen sensing element 50. A lead 120 to transmit a heating current from the control unit 108 to this heater 116 extends through a tubular metal support 118. Indicated at 119 is an insulating material in the tubular support 118. The metal tube 114 is open-ended, so that a fractional portion of the air-fuel mixture enters this tube 114 and is ignited by the heater element 116, resulting in that the oxygen sensing element 50 is exposed to a combustion gas produced from the air-fuel mixture despite its installation in the induction passage 82. If the oxygen sensing element 50 of the concentration cell type is exposed to the unburned air-fuel mixture, it is impossible to detect the air/fuel ratio because an oxygen partial pressure in the air-fuel mixture is too high to allow the element 50 (which is an oxygen concentration cell) to generate an electromotive force of a variable and sufficiently high magnitude. The inlet opening of the metal tube 114 is provided with a wire screen 117 to prevent backfire.

Preferably, the heater element 116 is made of platinum which exhibits a catalytic activity on oxidation of hydrocarbons. Alternatively, a noncatalytic heater element (116) may be embedded or enclosed in a small mass of a catalytic substance.

Figure 4:
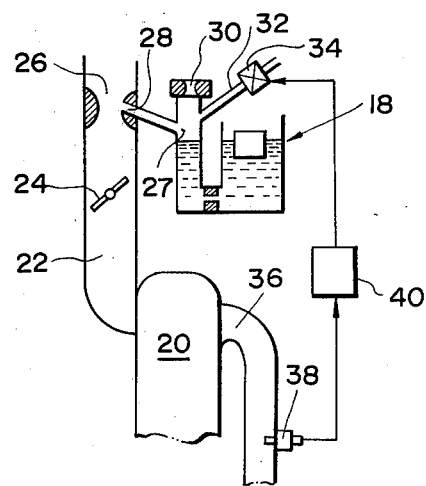
FIG. 4 is a schematic illustration of a conventional air/fuel ratio control system for an internal combustion engine.

As will be understood from a comparison between FIG. 4 and FIG. 8, the closed-loop in the feedback control system according to the invention is considerably shorter in overall length than that in the conventional control system of FIG. 4. Accordingly the "response lag" and "control lag" in the control system of the invention become considerably smaller than those in conventional control systems. The following Table 2 presents the result of an experiment conducted on the control system of FIG. 8 applied to the same engine as in the experiment the result of which was presented in Table 1. The target of the control was a stoichiometric air/fuel ratio. (In Table 2, the data for the conventional control system were transferred from Table 1.)

TABLE 2

| Direction of Change of Air-Fuel Mixing Ratio | Time Lag Low (Rich) → High (Lean) | |
|---|---|---|
| | Conventional Control System | Control System of the Invention |
| control unit-EM valve | 6 ms | 6 ms |
| EM valve-main fuel nozzle | 4 ms | 4 ms |
| main nozzle-intake valve waiting for opening of intake valve | 15 ms 0-60 ms | 15 ms 0-60 ms |
| combustion chamber | 32 ms | 0 |
| exhaust valve-O$_2$—sensor | 6 ms | 0 |
| response of O$_2$—sensor | 20 ms | 20 ms |
| total "response lag" | 143 ms (max.) | 105 ms (max.) |
| time required to correct deviated mixing ratio to stoichiometric ratio by continuing correcting process | about 250 ms | about 185 ms |
| total "control lag" | about 393 ms (max.) | about 290 ms (max.) |

As demonstrated by the data in Table 2, the present invention achieves about 20 percent shortening of total "control lag" compared with the conventional feedback control systems including an oxygen sensor installed in the exhaust system. Accordingly, in the case of applying the present invention to an engine equipped with a carburetor the responsiveness becomes comparable to that in the case of providing a fuel injection valve to each intake port. In a feedback control system according to the invention, oscillatory fluctuations of the air/fuel ratio as illustrated in FIG. 1 become considerably smaller, and the range of fluctuations of the air/fuel ratio becomes about ±0.2, or smaller, with respect to an intended air/fuel ratio.

The above illustrated embodiment relates to a fuel system using a carburetor, but the present invention is also applicable to a fuel injection system with the possibility of further shortening the "control lag".

The sensor of FIGS. 5 and 7 is unquestionably advantageous over the conventional sensor of FIG. 1. However, when this advanced sensor is made to exhibit a slope output characteristic as represented by the curve A or curve B of FIG. 6 there is a matter of inconvenience that an output voltage value does not correspond to only one definite air/fuel ratio value. In the case of curve A, for example, the output voltage becomes $V_{01}$ not only when the air/fuel ratio is 16.5 (at point P in curve A) but also when the air/fuel ratio is 14.7 (stoichiometrical, at point Q in curve A). If the target value of the air/fuel ratio control is 16.5, there is the possibility of making an erroneous judgement that the target value is reached although a true air/fuel ratio is 14.7. In the case of curve B, the output voltage becomes $V_{02}$ when the air/fuel ratio is either 13.5 (at point R) or 14.5 (nearly stoichiometrical, at point S). It is possible to construct a control circuit having the ability of discriminating, for example, between point P and point Q since point P is in the gently sloping portion of curve A whereas point Q is in the steeply varying portion around the stoichiometric air/fuel ratio. However, the present invention proposes to remove this inconvenience by a more practical and reliable technique.

When the target of air/fuel ratio control according to the invention is an air/fuel ratio either above or below the stoichiometric ratio, it is preferred that the control system of the invention has two oxygen-sensitive air/fuel ratio sensors both disposed in the induction passage. One of the two sensors (first sensor) corresponds to the sensor 110 in the control system of FIG. 8 and in this case is made to exhibit a slope output characteristic. The other (second sensor) is a sensor of the oxygen concentration cell type which is made to exhibit an on-off output characteristic of a type as represented by the curve of FIG. 2 in a combustion gas. Therefore, the second sensor may be either an advanced sensor as shown in FIGS. 5 and 7 or a conventional sensor such as the sensor 10 shown in FIG. 1. In any case, the second sensor must be arranged so as to be exposed to a combustion gas within the induction passage and located close to the first sensor. For example, the second sensor may be disposed in the metal tube 114 in the system of FIGS. 8 and 9 in combination with the first sensor 50 or may alternatively be disposed in a separate metal tube which is located close to the first tube 114 and contains an ignition means corresponding to the heater element 116 in the first tube 114. The output of the first sensor and the output of the second sensor are supplied simultaneously to a single control circuit including a discriminating circuit as described hereinafter.

Figure 10:
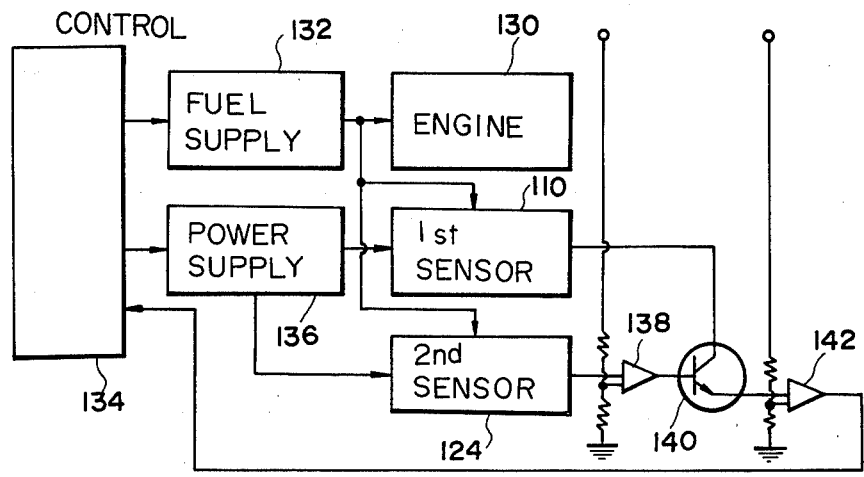
FIG. 10 is a block diagram of an air/fuel ratio control system embodying the present invention.

FIG. 10 shows the use of two oxygen sensitive air/fuel ratio sensors 110 and 124 in a feedback control system according to the invention which is applied to an engine 130 operated with a rich mixture and designed to maintain an air/fuel ratio (e.g. 13.5) below the stoichiometric ratio. The two sensors 110 and 124 are both installed in the induction passage as explained above. Indicated at 134 is a control circuit which provides a control signal to an air-fuel proportioning means 132 comprising an actuator such as an electromagnetic valve to vary the rate of fuel feed either directly or by admission of a variable quantity of auxiliary air into fuel. A power supply circuit 136 supplies a constant DC current of an adequate intensity to the first sensor 110 of the type as shown in FIG. 5 so as to make this sensor 110 exhibit a slope output characteristic as represented by the curve B of FIG. 6. The second sensor 124 exhibits an on-off type output characteristic as represented by the curve of FIG. 2. When the second sensor 124 too is of the type as shown in FIG. 5, the power supply circuit 136 supplies a constant DC current of a sufficiently high intensity to this sensor 124.

As a part of the control circuit 134, there is a discriminating circuit having a transistor 140 and amplifiers 138 and 142. The output of the first sensor 110 is supplied to the collector of the transistor 140, while the output of the second sensor 124 is applied to the base of the transistor 140 via the amplifier 138.

Assume that a desirably rich mixture is flowing in the induction passage so that the output voltage $V_{O2}$ of the first sensor 110 is produced at point R in the curve B. Then the output of the second sensor 124 is at the maximally high level. Accordingly the base potential of the transistor 140 becomes high, and this transistor 140 is in the conducting state. Therefore, the output voltage $V_{O2}$ of the first sensor 110 is transmitted to the main part of the control circuit 134, which can produce an appropriate control signal based on this voltage $V_{O2}$. When a nearly stoichiometrical air-fuel mixture is flowing in the induction passage so that the output voltage $V_{O2}$ of the first sensor 110 is produced at point S in the curve B, the output of the second sensor 124 is below the maximally high level so that the transistor 140 is in the non-conducting state. As a consequence the output voltage $V_{O2}$ of the first sensor 110 is not supplied to the main part of the control circuit 134. Then the control circuit 134 makes a judgement that the actual air/fuel ratio is above the target value and continues to command the air-fuel proportioning means 132 to increase the rate of fuel feed, until the transistor 140 becomes conducting to resume transmission of the output of the first sensor 110 to the control circuit 134.

Figure 11:
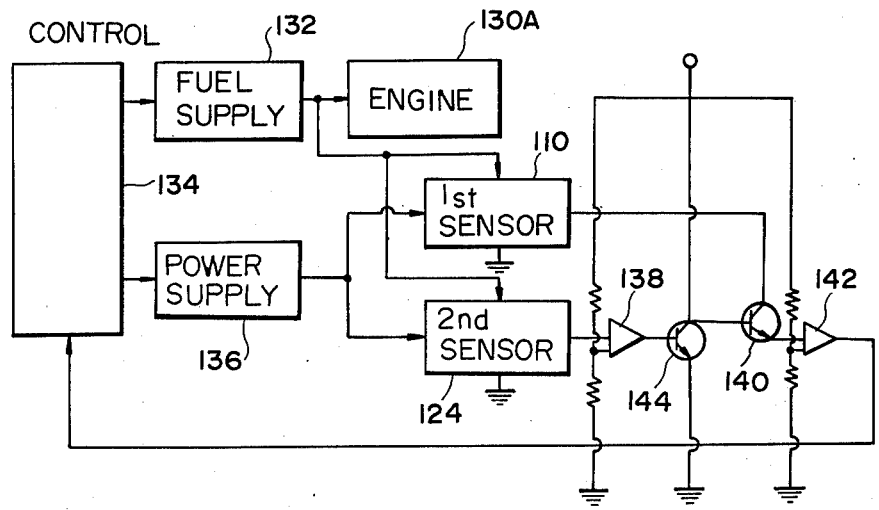
FIG. 11 is a block diagram showing a modification of the system of FIG. 10.

FIG. 11 shows the application of a similar feedback control system to an engine 130A operated with a lean mixture. In this system a discriminating circuit is constructed by adding a transistor 144 to the discriminating circuit of FIG. 10, and the output of the second sensor 124 is applied to the base of this transistor 144. The collector of the transistor 144 is connected to the base of the transistor 140 such that a source voltage is applied to the base of the transistor 140 when the transistor 144 is non-conducting.

Assume that a desirably lean mixture is flowing in the induction passage so that the output voltage $V_{O1}$ of the first sensor 110 is produced at point P in curve A of FIG. 6. Then the output of the second sensor 124 is at the minimally low level, so that the transistor 144 is in the non-conducting state. Accordingly the source voltage is applied to the base of the transistor 140 to make it conducting. As a consequence the output voltage $V_{O1}$ of the first sensor 110 is transmitted to the main part of the control circuit 134. When an approximately stoichiometrical air-fuel mixture is flowing in the induction passage so that the output voltage $V_{O1}$ of the first sensor 110 is produced at point Q in curve A, the output of the second sensor 124 is above the minimally low level so that the transistor 144 becomes conducting. Then the transistor 140 becomes non-conducting and interrupts the transmission of the output voltage $V_{O1}$ of the first sensor 110 to the main part of the control circuit 134.

The power supply circuit 136 and the control circuit 134 in FIGS. 10 and 11 may preferably be constructed such that the intensity of the current supplied to the first sensor 110 is temporarily varied according to operating conditions of the engine. When, for example, the engine is operated under an accelerating condition or full-throttle condition and requires the feed of a considerably rich mixture (e.g. mixture having an air/fuel ratio of about 13.5), it is suitable to augment the current intensity to about 10 $\mu$A thereby to raise the output level of the first sensor 110. When the engine requires a slightly rich mixture (e.g. mixture having an air-fuel ratio of about 14.5), a suitable current intensity will be about 5 $\mu$A.

In the case of using two oxygen-sensitive air/fuel ratio sensors in a control system of the invention, that is, one exhibiting a slope output characteristic and the other exhibiting an on-off type output characteristic, it is convenient that both the two sensors are of the type as illustrated in FIG. 5 and it is still more convenient that the two sensors are united into a single device.

Figure 12:
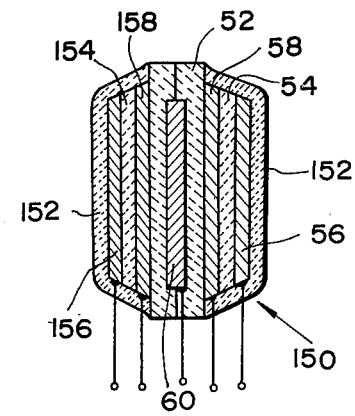
FIG. 12 is a schematic and sectional view of a combined oxygen sensing element which exhibits two different types of output characteristics and is of use in the present invention.

FIG. 12 shows a double-cell oxygen-sensitive element 150 which is obtained fundamentally by the addition of an oxygen concentration cell to the oxygen-sensitive element 50 of FIG. 5. On the uncovered side of the substrate 52 in the element 50 of FIG. 5, a reference electrode layer 158, a microscopically porous solid electrolyte layer 154 and a porous measurement electrode layer 156 are formed one upon another generally symmetrically with the corresponding layers 58, 54 and 56 on the other side of the substrate 52. After provision of leads to the electrode layers, the outer surfaces of the two concentration cells are entirely coated with a porous protective layer 160.

Figure 13:
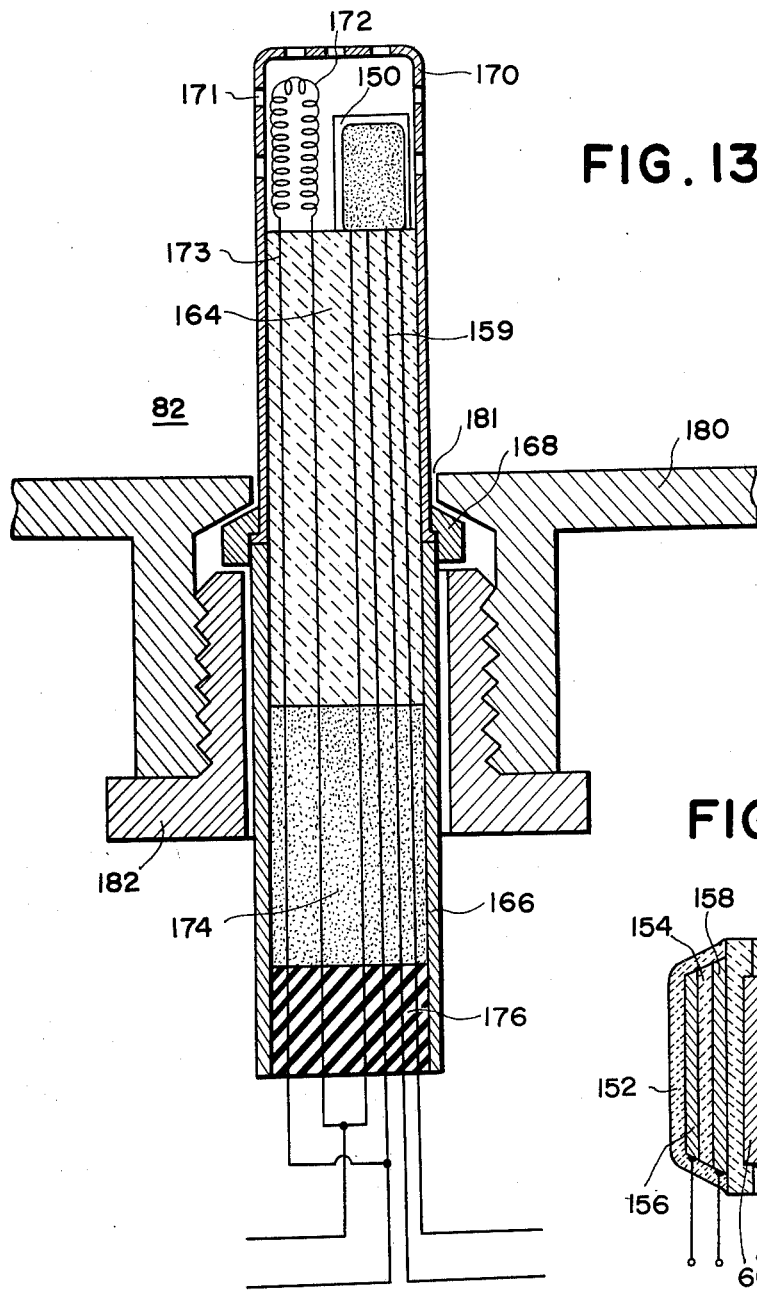
FIG. 13 is a schematic and sectional view of a principal part of an air/fuel ratio detection device comprising the oxygen sensing element of FIG. 12.

FIG. 13 shows an air/fuel ratio sensor assembly utilizing the double-cell element 150 of FIG. 12. The double cell element 150 is mounted on one end of a cylindrical rod 164 of mullite which is tightly received in a stainless steel holder 166. The mullite rod 164 is formed with axial bores through which extend leads 159 of the element 150. A rear section of the interior of the holder 166 is filled with an insulating and heat-resistant material 174 such as powdered alumina, and the rear end of the holder 166 is closed with a plug 176 of a synthetic resin. In place of the metal tube 114 in FIG. 9, a cylindrical hood 170 of stainless steel is fitted to the mullite rod 164 and weld-bonded to the holder 166 by using a ring member 168 such that the element 150 is enclosed in an end portion of this hood 170. In this end portion, the hood 170 is formed with a plurality of holes 171 which serve as gas inlets and gas outlets. In the interior of the hood 170 a platinum heater element 172 is positioned close to the oxygen-sensitive element 150, and leads 173 of this heater element 170 extend through axial bores in the mullite rod 164. A front end portion of the thus assembled sensor is inserted into the induction passage 82 through a hole 181 formed in the wall 180 of the induction pipe and secured to the wall 180 by the use of a cap nut 182.

One of the two concentration cells of the element 150 is made to exhibit a slope output characteristic by the application of a DC current of the adequate intensity, while the other cell is made to exhibit an on-off type output characteristic by the application of a DC current of a higher intensity.

The target value of air/fuel ratio control according to the invention is determined primarily according to the type of exhaust-purifying means provided to the engine.

Figure 14:
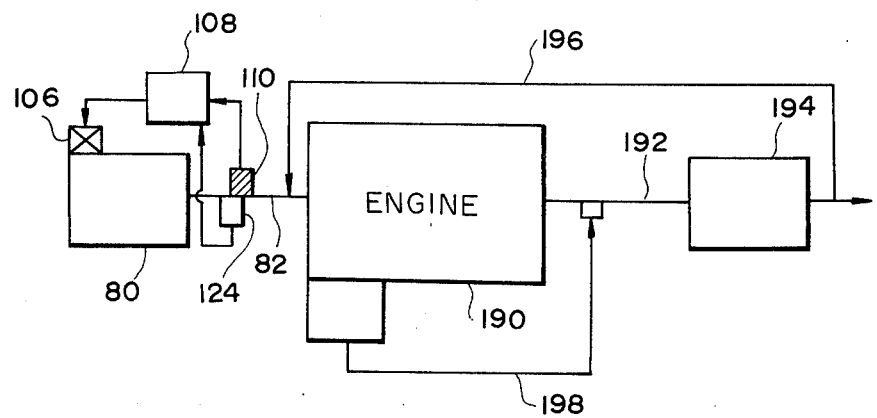
FIGS. 14 and 15 are respectively block diagrams of two internal combustion engine systems both provided with an air/fuel ratio control system according to the invention.

FIG. 14 shows an engine system including a catalytic converter 194 containing an oxidation catalyst, an exhaust gas recirculation circuit 196 and a secondary air supply circuit 198 connected to exhaust passage 192. In this case, it is desirable to perform the feedback control so as to control the air-fuel mixing ratio in the carburetor 80 to about 13.5, meaning the supply of a considerably rich mixture to combustion chambers 190 of the engine. Since a considerably high rate of exhaust gas recirculation is necessary in this type of engine system to supress the formation of NOx, if a lower air/fuel ratio is employed it becomes impossible to maintain stable operation of the engine. On the other hand, the removal of CO and HC by the oxidation catalyst is not efficiently achieved when a rich mixture is employed. Therefore, secondary air is introduced into the exhaust passage 192 through the circuit 198 such that the diluted exhaust gas entering the catalytic converter 194 becomes to correspond to an exhaust gas produced by combustion of a lean mixture. The catalytic converter 194 may be replaced by a thermal reactor. Then it becomes desirable to control the air-fuel mixing ratio in the carburetor 80 to a still lower value such as about 12.5. The secondary air supply circuit 198 is utilized such that the weight ratio of the sum of the air contained in the rich mixture and the secondary air to the fuel contained in the rich mixture becomes about 16.5. The first air/fuel ratio sensor 110 in the engine system of FIG. 14 is made to exhibit the slope output characteristic represented by curve B of FIG. 6.

Figure 15:
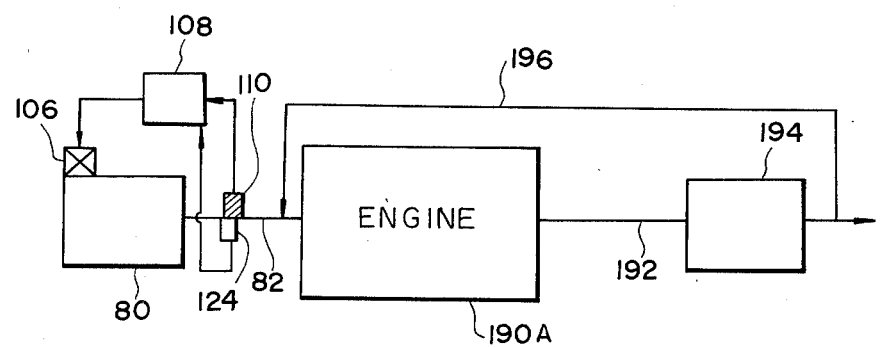

In an engine system shown in FIG. 15, the engine has advanced type of combustion chambers 190A featuring an improved combustion characteristic, so that stable and efficient engine operation can be maintained even though a considerably lean mixture and considerably high rate of exhaust gas recirculation are employed jointly. In this case, the feedback control according to the invention is performed so as to control the air/fuel ratio in the carburetor 80 to about 16.5 whether the exhaust purifying device 194 is a thermal reactor or a catalytic converter containing an oxidation catalyst. Because of the employment of such a lean mixture, the engine system of FIG. 15 does not need a secondary air supply circuit. The first air/fuel ratio sensor 110 in the system of FIG. 15 is made to exhibit the slope output characteristic represented by curve A of FIG. 6.

Thus, the present invention makes it possible to perform feedback control of air/fuel ratio even when either a rich mixture of a lean mixture considerably deviated from a stoichiometric mixture is employed. Accordingly, even when an exhaust gas purifying means other than three-way catalyst is employed it becomes possible to achieve efficient purification of exhaust gas without sacrificing the output or fuel economy of the engine.

The present invention can be applied also to advanced types of internal combustion engines such as lean-burn engines having combustion chambers each formed with an antechamber, quick-burn engines having combustion chambers each equipped with two spark plugs and performing a very high rate of exhaust gas recirculation by using a slightly rich mixture to maintain good driveability, engines provided with a catalytic converter containing three-way catalyst and an altitude compensation system, and electronically controlled engines utilizing a microcomputer to widely variably control the air/fuel ratio in dependence on engine operating conditions, and in every case the control of air/fuel ratio can be accomplished with improved precision and responsiveness.

What is claimed is:

1. A control system for feedback control of the mixing ratio of an air-fuel mixture in an induction passage for an internal combustion engine, the control system comprising:
   an electrically controllable fuel supply means for supplying fuel into the induction passage;
   a first oxygen-sensitive air/fuel ratio sensor which has an oxygen ion conductive solid electrolyte layer and two electrode layers formed on the solid electrolyte layer and is disposed in the induction passage in a section downstream of the fuel supply means;
   a second oxygen-sensitive air/fuel ratio sensor disposed in said section of the induction passage so as to be located close to said first air/fuel ratio sensor, said second sensor having an oxygen ion conductive solid electrolyte layer with two electrode layers formed thereon and exhibiting an on-off type output characteristic such that the magnitude of the output of said second sensor undergoes a sharp change between a maximally high level and a minimally low level when the air-fuel ratio of said mixture changes across a stoichiometric air/fuel ratio;
   a control means for providing a control signal to said fuel supply means based on a feedback signal produced by said first sensor to correct a deviation of the air-fuel mixing ratio indicated by the feedback signal from a predetermined mixing ratio, said control means including a discriminating means for interpreting information in said feedback signal with reference to the output of said second sensor;
   an ignition means for burning a fractional portion of the air-fuel mixture flowing in the induction passage such that said first and second sensors are exposed to a combustion gas produced by combustion of said fractional portion of the air-fuel mixture; and
   a power supply means for forcing a constant DC current of a predetermined intensity to flow through said solid electrolyte layer of said first sensor between said two electrode layers thereby selectively affording said first sensor with one of (a) first type slope output characteristic such that the magnitude of the output of said first sensor gradually varies as the air-fuel mixing ratio varies but remains above said stoichiometric air/fuel ratio, and (b) second type slope output characteristic such that the magnitude of the output of said first sensor gradually varies as the air-fuel mixing ratio varies but remains below said stoichiometric air/fuel ratio.

2. A control system according to claim 1, wherein said solid electrolyte layer of said first air/fuel ratio sensor is a microscopically porous layer formed on a substantially flat substrate, a first one of said two electrode layers being a microscopically porous thin layer formed on the outer side of said solid electrolyte layer, the second one of said two electrode layers being a thin layer formed on the inner side of said solid electrolyte layer and, macroscopically, entirely shielded from an environmental atmosphere by said substrate and said solid electrolyte layer.

3. A control system according to claim 2, wherein said first air/fuel ratio sensor further comprises an electrical resistance heating means embedded n said substrate.

4. A control system according to claim 2, wherein said first air/fuel ratio sensor is electrically connected to said power supply means such that, when said predetermined mixing ratio is higher than said stoichiometric air/fuel ratio, said constant DC current is forced to flow in said first sensor through said solid electrolyte layer from said first one of said two electrode layers towards said second one of said two electrode layers, whereby said sensor exhibits said first type slope output characteristic.

5. A control system according to claim 2, wherein said first air/fuel ratio sensor is electrically connected to said power supply means such that, when said predetermined mixing ratio is lower than said stoichiometric air/fuel ratio, said constant DC current is forced to flow in said first sensor through said solid electrolyte layer from said second one of said two electrode layers towards said first one of said two electrode layers, whereby said sensor exhibits said second type slope output characteristic.

6. A control system according to claim 1, wherein said second sensor is generally similar in construction to said first sensor and connected to said power supply means such that another DC current is forced to flow through the solid electrolyte layer of said second sensor between the two electrode layers of said second sensor, the intensity of said another DC current being higher than the intensity of said DC current supplied to said first sensor.

7. A control system according to claim 6, wherein said substrate of said first sensor is made to serve also as the substrate of said second sensor.

8. A control system according to claim 7, wherein the solid electrolyte layer and the two electrode layers of said second sensor are formed on said substrate oppositely to the solid electrolyte layer and the two electrode layers of said first sensor.

9. A control system according to claim 1, wherein said discriminating means includes a switch means responsive to the output of said second sensor for passing the output of said first sensor.

10. A control system according to claim 9, wherein said switch means comprises a transistor having a collector connected to said first sensor for receiving the output of said first sensor and a base connected to receive the output of said second sensor.

11. A control system according to claim 9, wherein said switch means includes a first transistor having a base connected to receive the output of said second sensor and a collector; and a second transistor having a base connected to said collector of said first transistor and a collector connected to said first sensor for receiving the output of said first sensor.

* * * * *